United States Patent
Keusch et al.

(10) Patent No.: US 6,635,045 B2
(45) Date of Patent: *Oct. 21, 2003

(54) ELECTRODES AND METHOD FOR MANUFACTURING ELECTRODES FOR ELECTRICALLY ASSISTED DRUG DELIVERY

(75) Inventors: Preston Keusch, Hazlet, NJ (US); Uday K. Jain, Mahway, NJ (US); Vilambi Nrk Reddy, Tamil/Nadu (IN); Bruce M. Eliash, Franklin Lakes, NJ (US); Kevin John Carey, North Plainfield, NJ (US); Vitaly Falevich, Ozone Park, NJ (US)

(73) Assignee: Vyteris, Inc., Fair Lawn, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/897,698

(22) Filed: Jun. 29, 2001

(65) Prior Publication Data

US 2002/0062102 A1 May 23, 2002

Related U.S. Application Data

(63) Continuation-in-part of application No. 09/610,563, filed on Jun. 30, 2000.

(51) Int. Cl.$^7$ .................... A61M 31/00; A61N 00/30
(52) U.S. Cl. .................... 604/501; 604/20; 424/449
(58) Field of Search ............... 604/20, 501, 890.1, 604/62, 49; 607/153, 152, 149, 115; 424/449, 448, 78.12; 514/772

(56) References Cited

U.S. PATENT DOCUMENTS

| | | | | | |
|---|---|---|---|---|---|
| 4,474,570 | A | * | 10/1984 | Ariura et al. | 604/20 |
| 4,764,164 | A | * | 8/1988 | Sasaki | 604/20 |
| 5,084,008 | A | * | 1/1992 | Phills | 29/825 |
| 5,354,790 | A | * | 10/1994 | Keusch et al. | 252/500 |
| 5,443,442 | A | * | 8/1995 | Phipps et al. | 604/20 |
| 5,464,387 | A | * | 11/1995 | Haak et al. | 604/20 |
| 5,543,098 | A | * | 8/1996 | Myers et al. | 264/104 |
| 5,582,587 | A | * | 12/1996 | Gyory et al. | 604/20 |
| 5,618,265 | A | * | 4/1997 | Myers et al. | 604/20 |
| 5,647,844 | A | * | 7/1997 | Haak et al. | 424/449 |
| 5,766,144 | A | * | 6/1998 | Lai et al. | 604/20 |
| 5,837,281 | A | * | 11/1998 | Iga et al. | 424/449 |
| 5,882,677 | A | * | 3/1999 | Kupperblatt | 424/443 |
| 5,908,400 | A | * | 6/1999 | Higo et al. | 604/20 |
| 5,983,130 | A | * | 11/1999 | Phipps et al. | 604/20 |
| 5,990,179 | A | * | 11/1999 | Gyory et al. | 514/329 |
| 6,004,577 | A | * | 12/1999 | Murdock | 424/400 |
| 6,049,733 | A | * | 4/2000 | Phipps et al. | 424/449 |
| 6,064,908 | A | * | 5/2000 | Muller et al. | 604/20 |
| 6,071,508 | A | * | 6/2000 | Murdock | 424/449 |
| 6,295,469 | B1 | * | 9/2001 | Linkwitz et al. | 604/20 |
| 6,350,259 | B1 | * | 2/2002 | Sage et al. | 604/501 |
| 6,377,847 | B1 | | 4/2002 | Keusch et al. | |

FOREIGN PATENT DOCUMENTS

WO    WO 01/91848    12/2001

OTHER PUBLICATIONS

U.S. patent application Ser. No. 09/584,453, Bernhard et al., no date.

* cited by examiner

Primary Examiner—Henry Bennett
(74) Attorney, Agent, or Firm—Kirkpatrick & Lockhart LLP

(57) ABSTRACT

Provided is a method for loading electrode-corroding ingredients into an un-loaded donor gel reservoir of an electrode for an electrically assisted drug delivery system. The method provides that a salt, such as sodium chloride or an organic salt, is provided in the un-loaded donor gel reservoir, contrary to convention. Related electrically assisted drug delivery electrode assemblies also are provided.

19 Claims, 4 Drawing Sheets

ELECTRODES AND METHOD FOR MANUFACTURING ELECTRODES FOR ELECTRICALLY ASSISTED DRUG DELIVERY

This is a continuation-in-part of U.S. patent application Ser. No. 09/610,563, filed Jun. 30, 2000, which is incorporated herein by reference in its entirety.

BACKGROUND OF THE INVENTION

1. Field of the Invention

The present invention relates to electrodes for electrically assisted drug delivery and a method for manufacturing the electrodes.

2. Description of the Related Art

Transmembrane delivery, typically transdermal delivery, increasingly has become a favored route for delivery of many drugs or other active compounds. One common form of transmembrane delivery is passive transdermal delivery in which a patch containing a reservoir of drug(s) or other compound(s) is applied to a patient's skin. In passive transdermal drug delivery, a patch is suitably configured so that the compound will pass into, and commonly through, the patient's skin. Passive transmembrane delivery also can be used for delivery to or through other bodily membranes, such as mucosa. However, passive delivery is limited due to the barrier properties of the stratum corneum.

Delivery of active ingredients through membranes, such as, without limitation skin, mucous membranes and nails may be facilitated by the application of an electric potential across the membrane. Iontophoresis and electroendosmosis are two forms of electrically assisted delivery. Typically, iontophoresis and electroendosmosis occur simultaneously to varying relative degrees whenever an electric potential is applied to a membrane, depending on the contents of the electrode reservoir and tissue-side composition. However, when the active ingredient to be delivered is ionic and transport is mainly due to charge transfer, the method typically is referred to as iontophoresis. In electrically assisted delivery, a reservoir containing the active ingredient, typically a drug, is placed on an anode or a cathode electrode that is connected to a source of electricity, such as a battery. In use, the drug-containing anode or cathode, the active or donor electrode, is applied to a membrane of a patient. An opposite electrode, also known as the return electrode, also is applied to a membrane of a patient to complete an electrical circuit. When a current is applied, the drug in the reservoir is delivered across the membrane. When the active ingredient is delivered from the anode, the delivery method is termed "anodic." When the active ingredient is delivered from the cathode, the drug delivery method is termed "cathodic."

Electrically assisted delivery methods increasingly are considered for the delivery route of hydrophilic, large and charged molecules, as well as for peptides and proteins. The delivery can be localized or systemic. For instance, iontophoresis may be used for local delivery of anesthetics for IV catheterizations or for removal of skin lesions. However, systemic delivery is preferred for active ingredients such as hormones, insulin or pharmaceuticals such as opioids, nitroglycerine and nicotine.

PCT Patent publication WO 98/20869 discloses electrodes for the delivery of lidocaine and epinephrine. These active ingredients, being cationic under typical delivery conditions, are delivered from the anode reservoir. WO 98/20869 discloses an electrically assisted drug delivery system including an electric power supply, a donor anode and a return cathode. The anode contains a reservoir suitably configured to be in electrical contact with a patient's skin containing a composition including lidocaine, epinephrine, an antioxidant, such as sodium metabisulfite, and a metal chelator, such as EDTA. The return cathode contains a reservoir suitably configured to be in electrical contact with a patient's skin, containing a composition including sodium chloride and a buffer, such as a phosphate buffer.

One consideration in formulating compositions for iontophoretic drug delivery is that smaller, more mobile ions will decrease a given iontophoretic system's ability to deliver larger drug ions. Thus, convention dictates that donor electrode reservoirs contain a minimal amount of small ionic species that are not active ingredients but have the same (positive or negative) charge as the active ingredient(s) under drug delivery conditions. U.S. Pat. No. 5,573,503 recognizes the inefficiencies in iontophoretic drug delivery caused by the presence of competing small ionic species (see, column 3, lines 42–60). That patent describes a method for eliminating those competing ions by using, in one example, silver/silver chloride (Ag/AgCl) electrodes in anodic donor electrode assemblies.

Reservoirs of donor electrodes may be manufactured by mixing or impregnating the active ingredient into a suitable matrix that typically is a polymer hydrogel. The impregnated gel is applied as a layer to the electrode, such as a Ag/AgCl electrode printed onto a polymeric surface. Although this is a common method for preparing iontophoretic electrodes, it may not be a preferred method due to the desirability and long-term stability of electrodes that are not pre-loaded with drug(s). These unloaded gels are later loaded with drug(s) by absorption and diffusion. Manufacturing efficiencies arising from this method include: 1) the ability to store unloaded gels for longer times as compared to typical loaded gels, permitting production of comparatively larger lots of unloaded gels, and 2) the ability to load sub-lots of the unloaded gels at different times, with different active ingredients and/or with different concentrations of active ingredient(s). Nevertheless, the method suffers from certain limitations. The solution loading process can result in ionic concentration differences along the electrode at the gel-electrode interface. When the electrode is exposed to different chloride concentrations, a concentration cell is established resulting in an electrochemical reaction that consumes Cl⁻ and produces high concentrations of AgCl at certain sites and produces Ag and Cl⁻ at the other low concentration sites. This redistribution of Ag and AgCl is detrimental as it can decrease the electrode capacity available for drug delivery. In use, the electrode capacity of the electrode may be exceeded in certain areas causing hydrolysis and pH burns. Furthermore, this type of localized corrosion can lead to the isolation of the electrodes from the interconnect traces leading to early failure of the patch. An electrode reservoir that can be loaded with drug without suffering from the formation of localized sites of electrode corrosion is therefore desired.

SUMMARY OF THE INVENTION

It has now been found that inclusion of sodium chloride or other salts, including organic salts, in an unloaded donor (active) electrode reservoir, prevents electrode corrosion during and resulting from loading of drug reservoirs by absorption and diffusion.

Thus, the present invention is directed to a donor electrode assembly for electrically assisted methods for delivery of active ingredients to patients. The electrode assembly contains a donor reservoir having a sufficient amount of a salt, for instance an alkaline metal halide salt, such as sodium chloride, to inhibit electrode corrosion. Also provided is a method of manufacturing of iontophoretic electrodes in which electrodes comprising unloaded donor reservoirs containing a predetermined amount of a salt such as NaCl, are loaded with an active ingredient by absorption and diffusion. Typically, drug delivery is anodic and the active ingredient typically contains chloride ions. In one instance, the active ingredient is lidocaine HCl, which is delivered with epinephrine in ionic form. By including salt essentially homogeneously in the unloaded reservoir, corrosion of the electrode resulting from loading reservoirs with active ingredient(s) is prevented.

DETAILED DESCRIPTION

Figure 1:
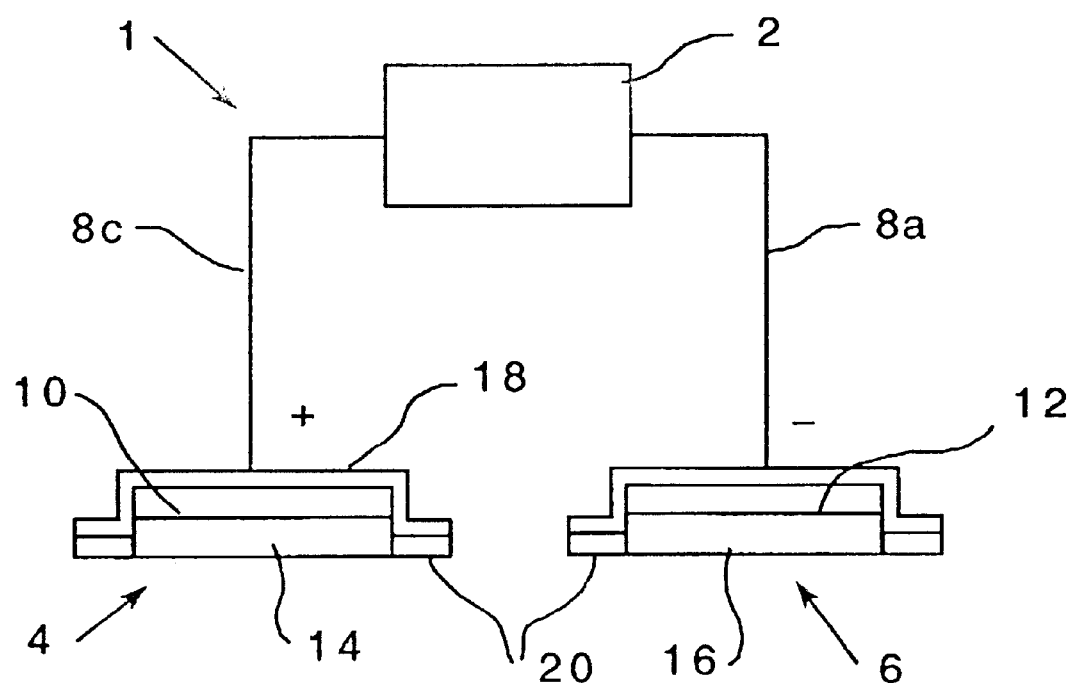
FIG. 1 shows schematically an electrically assisted drug delivery system including an anode assembly, a cathode assembly and a controller/power supply.

The use of numerical values in the various ranges specified in this application, unless expressly indicated otherwise, are stated as approximations as though the minimum and maximum values within the stated ranges were both preceded by the word "about". In this manner slight variations above and below the stated ranges can be used to achieve substantially the same results as values within the ranges. Also, the disclosure of these ranges is intended as a continuous range including every value between the minimum and maximum values.

Described herein is an electrode assembly for electrically assisted transmembrane delivery, typically iontophoretic delivery, of an active agent that exhibits essentially uniform conductivity over the surface of the electrode in contact with a membrane of a patient. Typical donor electrode reservoirs are substantially free from competing ions that are smaller than the ionic drug to be delivered and that interfere with the electrically assisted delivery process. However, in donor reservoirs of electrode assemblies prepared by certain methods, that are typically in contact with silver or silver/silver chloride electrodes, conductivity is far from uniform due to localized sites of higher and lower ionic strength formed during the drug loading and delivery process. In one such manufacturing process, an unloaded gel reservoir is placed on an electrode before loading the drug solution. This drug loading process typically leads to chloride concentration differences along the gel-electrode interface. If the electrode is exposed to different chloride concentrations, a concentration cell is formed, resulting in an electrochemical reaction that consumes chloride ions and produces AgCl at the high concentration sites, while Ag and Cl$^-$ are produced at the lower concentration sites. This redistribution has a detrimental impact on delivery of drugs from the gel and uniformity of charge over the gel-skin interface. This problem is solved in a manner in contrast to fundamental prior teachings, by including a salt such as sodium chloride or sodium acetate in the donor electrode reservoir before it is loaded.

By "unloaded reservoir," it is meant a drug reservoir, typically a hydrogel, as described in further detail below, that includes a hydrogel polymer composition, water and a salt. One or more additional ingredients may be included in the un-loaded reservoir, but not an active ingredient, or other electrode-corrosive ingredient that is to be loaded into the reservoir after the hydrogel is formed and assembled in an electrode assembly in contact with an Ag/AgCl electrode. Other additional non-ionic ingredients, such as preservatives, may be included in the unloaded reservoir.

Although the salt may be one of many salts, including organic salts, the salt typically is sodium chloride. Other salts such as, without limitation, KCl or sodium acetate might be equal to NaCl in terms of functionality, and may or may not be preferred in certain instances.

The term "electrically assisted delivery" refers to the facilitation of the transfer of any compound across a membrane, such as, without limitation, skin, mucous membranes and nails, by the application of an electric potential across that membrane. "Electrically assisted delivery" is intended to include, without limitation, iontophoretic, electrophoretic and electroendosmotic delivery methods. By "active ingredient," it is meant, without limitation, drugs, active agents, therapeutic compounds and any other compound capable of eliciting any pharmacological effect in the recipient that is capable of transfer by electrically assisted delivery methods.

FIG. 1 depicts schematically a typical electrically assisted drug delivery apparatus 1. Apparatus 1 includes an electrical power supply/controller 2, an anode electrode assembly 4 and a cathode electrode assembly 6. Anode electrode assembly 4 and cathode electrode assembly 6 are connected electrically to the power supply/controller 2 by conductive leads 8a and 8c. The anode electrode assembly 4 includes an anode 10 and the cathode electrode assembly 6 includes a cathode 12. The anode 10 and the cathode 12 are both in electrical contact with leads 8a and 8c. The anode electrode assembly 4 further includes an anode reservoir 14, while the cathode electrode assembly 6 further includes a cathode reservoir 16. Both the anode electrode assembly 4 and the cathode electrode assembly 6 include a backing 18 to which a pressure sensitive adhesive 20 is applied in order to affix the electrode assemblies 4 and 6 to a membrane, typically skin, so that reservoirs 14 and 16 are in electrical contact with the membrane. Optionally, reservoirs 14 and 16 can partially cover pressure sensitive adhesive 20.

Figure 2:
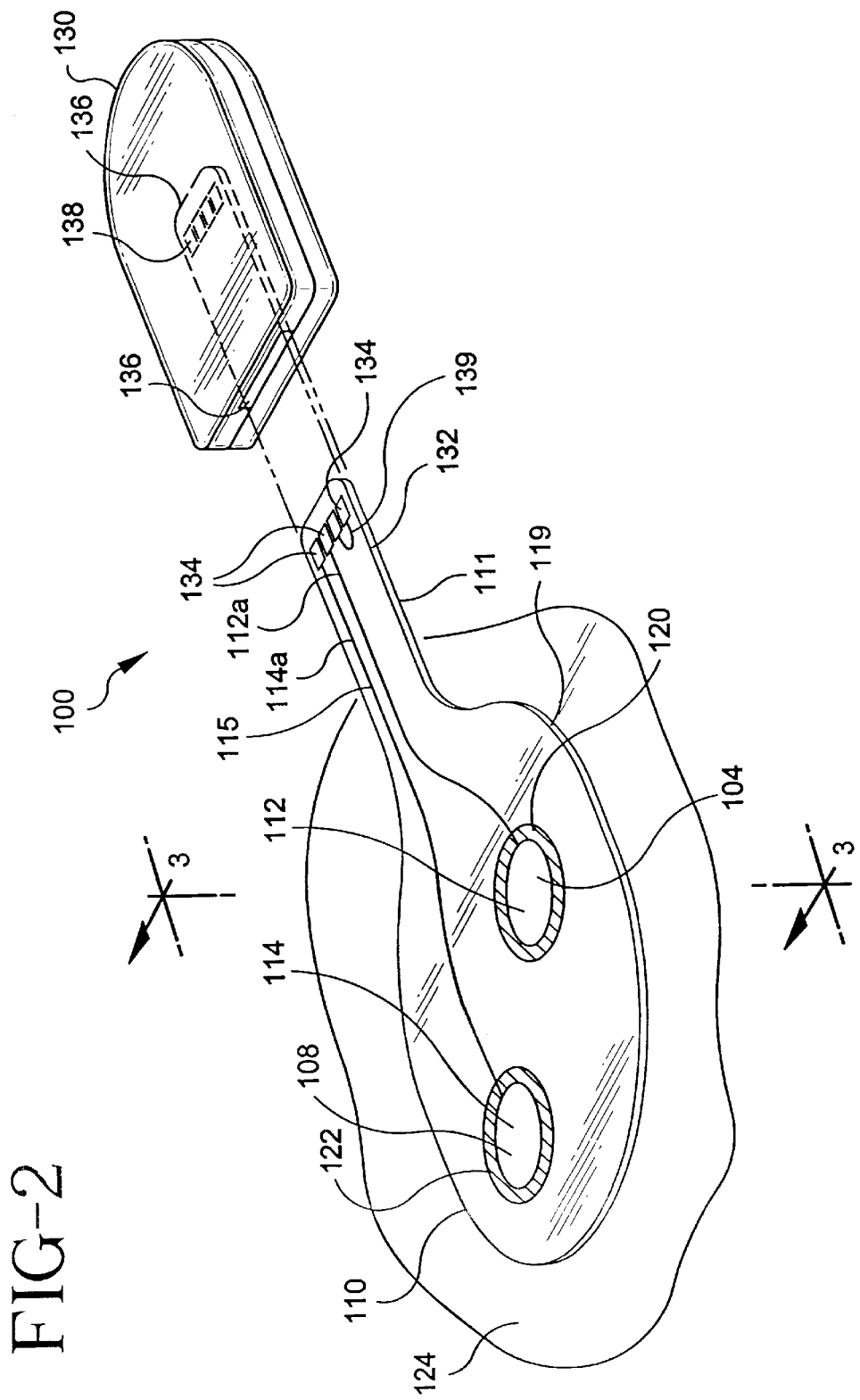
FIG. 2 shows a perspective view of an electrode/interconnect assembly.
Figure 3:
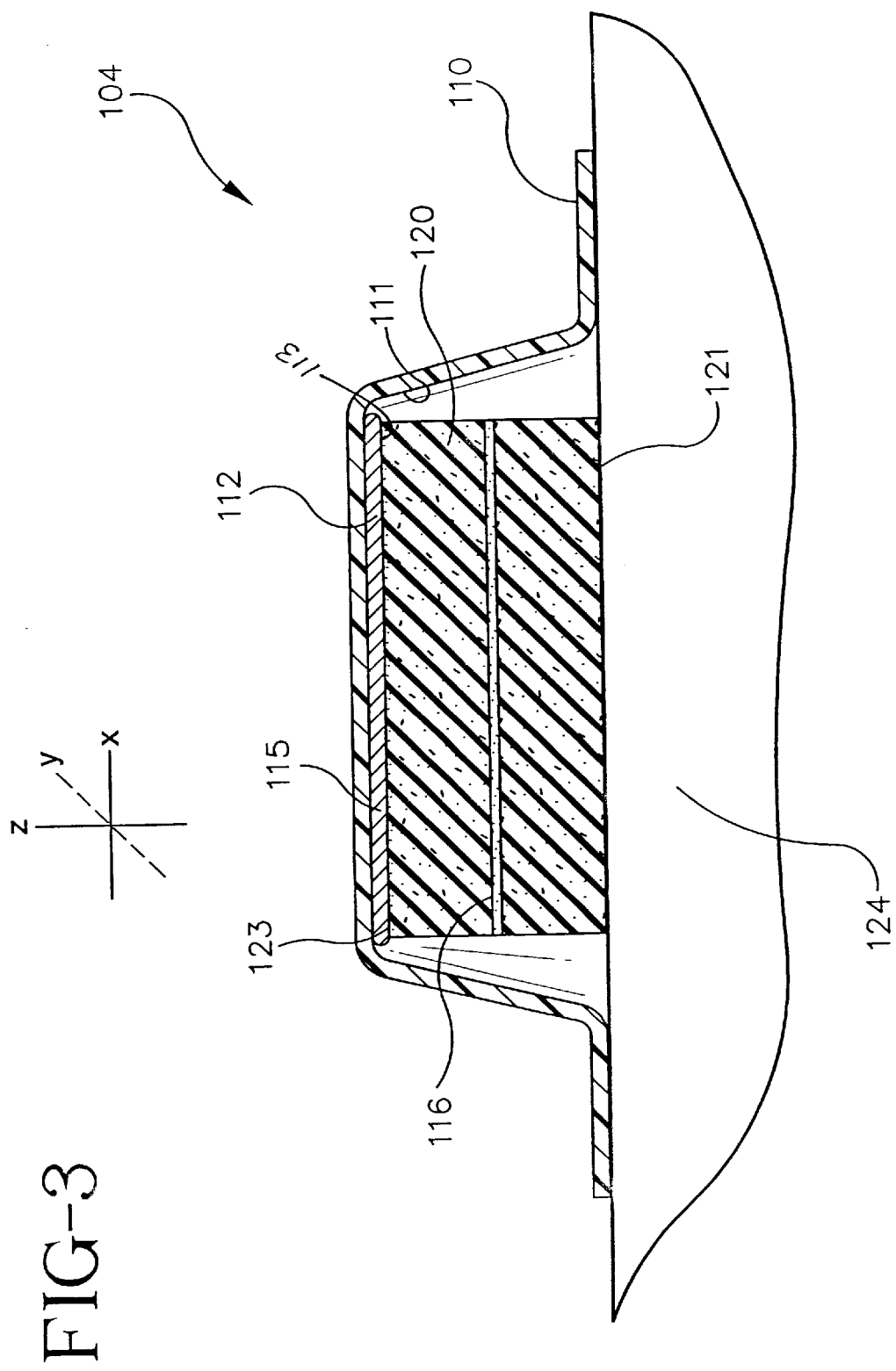
FIG. 3 shows a cross-section view of the anode reservoir-electrode as shown in FIG. 2.

FIGS. 2 and 3 show an iontophoretic device 100. Device 100 includes a first reservoir-electrode 104 (anode) charged with lidocaine HCl and epinephrine bitartrate and a second reservoir-electrode 108 intended to function as a cathode or return electrode as illustrated in FIG. 2. Device 100 includes a flexible backing 110 with first reservoir-electrode 104 and second reservoir-electrode 108 mounted thereon. Device 100 includes two electrodes, an anode 112 and a cathode 114, each having an electrode surface 113, and electrode traces 112a and 114a. Electrodes 112, 114 and electrode traces 112a and 114a are formed as a thin film deposited as traces onto flexible backing 110 with an inside surface 111. Typically, electrodes 112 and 114 and electrode traces 112a and 114a are formed from conductive ink 115 applied as a thin film to inside surface 111. Conductive ink 115 preferably includes silver and silver chloride in a suitable binder material. Electrodes 112 and 114 are each mounted with bibulous reservoirs, 120 and 122 respectively, formed from a cross-linked polymeric material such as cross-linked poly(vinylpyrrolidone) hydrogel that each include a substantially uniform concentration of a salt.

The cross-linked poly(vinylpyrrolidone) typically includes a reinforcement 116, preferably a low basis weight non-woven scrim to provide shape retention to the hydrogel. Reservoirs 120, 122 each have adhesive and cohesive properties that provide for a first surface 121, and a second surface 123. First surface 121 is typically releasably adherent to an applied area 124 of a patient's skin. Second surface 123 is adhesively adherent to electrodes 112 and 114. Typically, the bond strength of an adhesive bond formed between first surface 121 and applied area 124 of the patient's skin is less than the strength of an adhesive bond formed between second surface 123 and electrodes 112 and 114. Further, it is preferred that the strength of the releasable adhesive bond formed between first surface 121 and the patient's skin is less than the cohesive strength of the preferred reservoirs 120 and 122. These preferred adhesive and cohesive properties of reservoirs 120, 122 have the effect that when reservoir-electrodes 104, 108 of device 100 are removed from applied area 124 of the patient's skin, the reservoirs substantially cleanly come off patient's skin 124, leaving substantially no residue, stay substantially intact and do not come off of electrodes 112, 114 or backing 110.

Device 100 also includes a power supply 130 that supplies a preselected current or currents to the device when reservoir electrodes 104 and 108 are mounted on the patient's skin to form a completed circuit. Backing 110 includes an extended portion 132 with electrode traces 112a and 114a formed from conductive ink 115 extended thereon to connectors 134. Power supply 130 includes a receptacle 136 with mating connectors 138 to receive extended portion 132 and connectors 134. Extended portion 132 with connectors 134 allows power supply 130 to be refitted with fresh backings 110 having reservoir-electrodes 104 and 108 thereon. Power supply 130 and backing 110 includes a circuit 139 to identify the particular type of reservoir-electrodes and medicament to power supply 130.

In FIG. 3, a cross-sectional view of the anode reservoir-electrode 104 of device 100 is shown. In this view, anode reservoir-electrode 104 includes electrode 112 and an absorbent reservoir 120 having a substantially uniform concentration of salt situated in electrically conductive relation to electrode 112 at electrode surface 113. Absorbent reservoir 120 is formed from a hydrophilic material, such as a bibulous hydrophilic cross-linked polymeric material, that has a salt distributed essentially homogeneously therein. Bibulous hydrophilic cross-linked polymeric material of reservoir 120 has a first surface 121 and a second surface 123 that is adhesively adherent to electrode 112. First surface 121 of reservoir 120 is releasably adhesively adherent when applied to an area 124 of a patient's skin. Reservoir 120 has a cohesive strength and forms an adhesive bond with a bond strength between second surface 123 of the polymeric material to electrode 112 that is greater than the cohesive strength of the polymeric material. Additionally, an adhesive bond strength of first surface 121 of preferred polymeric reservoir 120 material to applied area 124 of the patient is less than the cohesive strength of polymeric reservoir 120 so that upon removal of reservoir-electrode 104 of the invention from applied area 124 of the patient, substantially no preferred polymeric reservoir 120 material remains on applied area 124 of the patient's skin and hydrophilic reservoir 120 remains substantially intact and adhesively adherent to electrode 112.

One material for forming hydrophilic reservoir 120 is a cross-linked poly(vinylpyrrolidone). The material is prepared as a viscous aqueous syrup that incorporates the selected salt in the desired concentration. In one embodiment of the invention, where the medicament to be delivered is lidocaine as the hydrochloride and epinephrine as the bitartrate, the active reservoir-electrode, i.e., containing the lidocaine and the epinephrine, is the anode because the medicaments being delivered are positive ions, the concentration of the sodium chloride is between about 0.001% wt. (% w/w) to about 1.0% wt. For other applications, other concentrations may be useful or preferred.

The donor electrode reservoir 120 is loaded with an active ingredient from an electrode reservoir loading solution by placing an aliquot of the loading solution directly onto the hydrogel reservoir and permitting the loading solution to absorb and diffuse into the hydrogel over a period of time.

Figure 4:
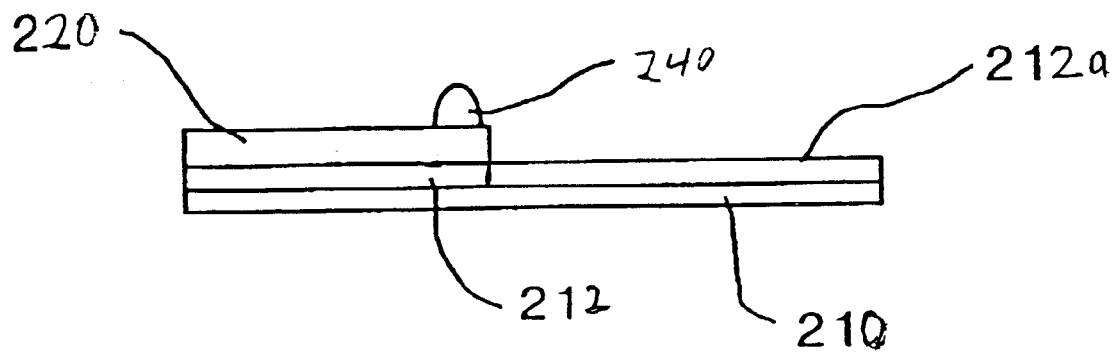
FIG. 4 shows an elevation view of a cross section of an un-loaded anode electrode assembly in contact with a loading solution.

FIG. 4 illustrates this method for loading of electrode reservoirs in which an aliquot of loading solution is placed on the hydrogel reservoir for absorption and diffusion into the reservoir. FIG. 4 is a schematic cross sectional drawing of an anode electrode assembly including an anode 212 and an anode trace 212a on a backing 210 and an anode reservoir 220 in contact with anode 212. An aliquot of a loading solution 240, containing any ingredients to be loaded into reservoir 220 is placed in contact with reservoir 220. Loading solution 240 is contacted with the reservoir 220 for a time period sufficient to permit a desired amount of the ingredients in loading solution 240 to absorb and diffuse into the gel reservoir 220.

In use, an electric potential is applied across a membrane to which the electrode reservoirs are in contact according to any profile and by any means for electrically assisted drug delivery known in the art. Examples of power supplies and controllers for electrically assisted drug delivery are well known in the art, such as those described in U.S. Pat. Nos. 6,018,680 and 5,857,994, among others. Ultimately, the optimal intensity and duration of the electric potential is empirically determined for any given electrode/electrode reservoir combination.

The anode and cathode reservoirs typically comprise a hydrogel. The hydrogel typically is hydrophilic and may have varying degrees of cross-linking and water content, as is practicable. A hydrogel as described herein may be any pharmaceutically and cosmetically acceptable absorbent hydrogel into which a loading solution and ingredients therein can be absorbed, diffused or otherwise incorporated and that is suitable for electrically assisted drug delivery. Suitable polymeric compositions useful in forming the hydrogel are known in the art and include, without limitation, polyvinylpyrrolidone (PVP), polyethyleneoxide, polyacrylamide, polyacrylonitrile and polyvinyl alcohols. The reservoirs may contain additional materials such as, without limitation: preservatives; antioxidants, such as sodium metabisulfite; chelating agents, such as EDTA; and humectants. As used herein in reference to the water component of the electrode reservoirs, the water is purified and preferably meets the standard for purified water in the USP XXXIII.

The donor (anode) reservoir also includes a salt, for instance a halide salt such as sodium chloride in a concentration of from about 0.001 wt. % to about 1.0 wt. %, preferably from about 0.06 wt. % to about 0.9 wt. % (wt. % is provided herein in reference to sodium chloride, and may vary for other salts in a substantially proportional manner depending on a number of factors, including the molecular weight and valence of the ionic constituents of each given salt in relation to the molecular weight and valence of sodium chloride). Other salts, such as organic salts, are useful in ameliorating the corrosive effects of certain drug salts. Typically the best salt for any ionic drug will contain an ion that is the same as the counter ion of the drug. For instance, acetates would be preferred when the drug is an acetate form.

The return (cathode) reservoir may be a hydrogel with the same or different polymeric structure as the donor (anode) reservoir and typically contains a salt, a preservative, an antioxidant and a humectant. Depending upon the ultimate manufacturing process, certain ingredients may be added during polymerization of the hydrogel reservoir, while others may be post-loaded as described above. Nevertheless, with respect to the charging or loading of either the donor or the return electrode reservoirs, it should be recognized that irrespective of the sequence of addition of ingredients, salt must be present in the reservoir and substantially evenly distributed therethrough prior to the loading of electrode-corrosive active ingredient(s).

For purposes of the present invention, preventing chloride cell formation and thereby preventing electrode corrosion, the active ingredient typically contains chloride ions. For instance, any active ingredients that are hydrochloride salts, suitable for electrically assisted transmembrane delivery, would benefit from the inclusion of salt such as NaCl in the hydrogel prior to loading. As described herein, Lidocaine HCl is one suitable active ingredient, preferably combined with epinephrine to elicit a desired pharmacological response. If the counterion of the drug is not chloride, a corrosion-inhibiting amount of that other counterion must be present in the unloaded reservoir to prevent corrosion of the electrode. If more than one counterion is present, such as in the case where more than one drug is loaded and each drug has a different counterion, it may be preferable to include sufficient amounts of both counterions in the reservoir to prevent electrode corrosion. It should be noted that in the examples provided below, the amount of epinephrine bitartrate loaded into the gel is not sufficient to cause corrosion.

Hydrogel reservoirs typically include a layer of scrim to facilitate ease of handling during patch assembly and to prevent distortion of the hydrogel during loading, thereby preventing uneven drug delivery over the surface of the electrode. Scrim may be a fabric or a nonwoven polymeric layer as described in U.S. Pat. Nos. 4,684,558, 4,706,680, 4,777,954 and 6,038,464, each of which is incorporated herein by reference in its entirety. Suitable electrode assemblies and methods of manufacture and loading thereof are described in additional detail in U.S. patent application Ser. No. 09/328,329, filed Jun. 9, 1999, which is incorporated herein by reference in its entirety.

EXAMPLE

Evaluation of the Effects of NaCl on Electrode Corrosion

Unloaded gel reservoirs were prepared as follows:

| Ingredient | Mg/patch |
|---|---|
| PVP | 24% wt. ± 1% wt. |
| Phenonip antimicrobial (phenoxy ethanol and parabens) | 1% wt. ± 0.05% wt. |
| NaCl | 0.0% wt., 0.06% wt. or 0.9% wt. |
| Purified water | QS |

The gels were crosslinked by electron beam irradiation to a radiation dose of about 2.5 Mrad (25 kGy) at 1 MeV electron voltage.

Loading Solution A was prepared from the following ingredients.

| Ingredient | Loading Solution (Formulation A; % wt.) |
|---|---|
| Lidocaine hydrochloride | 30 |
| L-epinephrine bitartrate | 0.5725 |
| NaCl | 0.06 |
| Disodium EDTA | 0.03 |
| Citric acid | 0.06 |
| Glycerin | 30 |
| Sodium metabisulfite | 0.15 |
| Purified Water | QS |

Fifteen unloaded PVP anode gel reservoirs (0.8 mL) were prepared, five with 0.0% wt. NaCl, five with 0.06% wt. NaCl and five with 0.9% wt. NaCl. The unloaded gel reservoirs were placed on Ag/AgCl anodes and were loaded by placing 0.32 mL of Loading Solution on the gel, as shown in FIG. 5. The Loading Solution was left on the gel reservoirs for 48 hours. After 48 hours, the electrodes were examined for signs of concentration effects as noted by discoloration (blackening) of the electrode surface. Table C summarizes the results of this experiment. The samples that exhibited visual signs of AgCl accumulation were designated "Yes," while those samples that did not show visual signs of AgCl accumulation were designated "No."

TABLE C

| | NaCl Concentration in the Initial Gel | | |
|---|---|---|---|
| Sample # | 0% wt. | 0.06% wt. | 0.9% wt. |
| 1 | Yes | No | No |
| 2 | Yes | No | No |
| 3 | Yes | No | No |
| 4 | Yes | No | No |
| 5 | Yes | No | No |

All five of the anode patches made with gels containing 0% wt. initial NaCl showed dark areas on the electrode surface underneath the area where the drug solution was initially loaded. The dark area on the electrode surface suggests that the anode was oxidized from $Ag+Cl^- \rightarrow AgCl + e^-$ in this region. This is caused by a $Cl^-$ concentration gradient along the electrode-reservoir surface. This concentration gradient causes a galvanic driving force large enough to form local AgCl deposits. The addition of as little as 0.06% wt. of NaCl is sufficient to inhibit oxidation of the Ag/AgCl electrode. Subsequent analysis indicates that as little as 0.001% wt. NaCl is needed to prevent corrosion of the electrode under typical gel loading conditions.

Whereas particular embodiments of the invention have been described herein for the purpose of illustrating the invention and not for the purpose of limiting the same, it will be appreciated by those of ordinary skill in the art that numerous variations of the details, materials and arrangement of parts may be made within the principle and scope of the invention without departing from the invention as described in the appended claims.

What is claimed is:

1. A method for making an electrode assembly for electrically assisted transmembrane delivery of an active ingredient, comprising the steps of:

a. providing an unloaded electrode assembly comprising a Ag/AgCl electrode and a reservoir comprising a polymer having an aqueous composition dispersed therein, the aqueous composition comprising an amount of salt effective to inhibit electrode corrosion; and b. contacting a surface of the reservoir with an aqueous loading solution comprising an active electrode-corrosive ingredient for an amount of time effective to permit loading of a predetermined amount of the active electrode-corrosive ingredient into the reservoir.

2. The method of claim 1, wherein the salt contains an ion that is the same as a counterion of said active electrode-corrosive ingredient.

3. The method of claim 1, wherein the electrode-corrosive ingredient comprises chloride ions.

4. The method of claim 1, wherein the electrode-corrosive ingredient is a drug.

5. The method of claim 1, wherein the electrode-corrosive ingredient is a hydrochloride salt.

6. The method of claim 1, wherein the electrode-corrosive ingredient is lidocaine HCl.

7. The method of claim 6, the aqueous solution further comprising epinephrine.

8. The method of claim 1, wherein the loading solution is applied to the reservoir as one or more droplets.

9. The method of claim 1, wherein the reservoir comprises a polyvinylpyrrolidone hydrogel.

10. The method of claim 1, in which the loading solution comprises:
about 30% wt. lidocaine HCl;
about 0.57% wt. L-epinephrine bitartrate; and
about 0.06% to about 0.9% wt. NaCl.

11. The method of claim 10, in which the loading solution further comprises a chelating agent; a humectant, and an antioxidant.

12. The method of claim 1, wherein the reservoir comprises about 24% wt. ±1% wt. of a polyvinylpyrrolidone hydrogel and about 0.06% wt. NaCl and wherein the reservoir is contacted with about 33% wt. ±10% wt. of a loading solution, comprising:
about 30% wt. lidocaine HCl;
about 0.57% wt. L-epinephrine bitartrate; and
about 0.06% wt. to about 0.9% wt. NaCl.

13. The method of claim 12, wherein the loading solution further comprises:
about 0.03% wt. EDTA;
about 0.06% wt. citric acid;
about 30% wt. glycerin; and
about 0.15% wt. sodium metabisulfite.

14. The method of claim 1 in which the loading solution comprises:
about 30% wt. lidocaine HCl;
about 0.57% wt. L-epinephrine bitartrate;
about 0.06% wt. NaCl;
about 0.03% wt. EDTA;
about 0.06% wt. citric acid;
about 30% wt. glycerin; and
about 0.15% wt. sodium metabisulfite.

15. An electrode prepared according to a process for preparing the electrode comprising the steps of:

a. providing an unloaded electrode assembly comprising a Ag/AgCl electrode and a reservoir comprising a polymer having an aqueous composition dispersed therein, the aqueous composition comprising an amount of salt effective to inhibit electrode corrosion; and b. contacting a surface of the reservoir with an aqueous loading solution comprising an active electrode-corrosive ingredient for an amount of time effective to permit loading of a predetermined amount of the active electrode-corrosive ingredient into the reservoir.

16. The electrode of claim 15, wherein the reservoir comprises about 24% wt. ±1% wt. of a polyvinylpyrrolidone hydrogel and about 0.06% wt. NaCl and wherein the reservoir is contacted with about 33% wt. ±10% wt. of a loading solution, comprising:
about 30% wt. lidocaine HCl;
about 0.57% wt. L-epinephrine bitartrate; and
about 0.06% wt. to about 0.9% wt. NaCl.

17. the electrode of claim 15, in which the loading solution further comprises a chelating agent, a humectant and an antioxidant.

18. The electrode of claim 15, wherein the loading solution comprises:
about 30% wt. lidocaine HCl;
about 0.57% wt. L-epinephrine bitartrate; and
about 0.06% wt. NaCl.

19. The electrode assembly of claim 18, wherein the loading solution further comprises:
about 0.03% wt. EDTA;
about 0.06% wt. citric acid;
about 30% wt. glycerin; and
about 0.15% wt. sodium metabisulfite.

\* \* \* \* \*

UNITED STATES PATENT AND TRADEMARK OFFICE
CERTIFICATE OF CORRECTION

PATENT NO. : 6,635,045 B2
DATED : October 21, 2003
INVENTOR(S) : Preston Keusch et al.

It is certified that error appears in the above-identified patent and that said Letters Patent is hereby corrected as shown below:

Title page,
Item [56], References Cited, U.S. PATENT DOCUMENTS, insert the following patents:

-- 6,496,727    12/2002    Bernhard et al.
5,362,308       11/1994    Chien et al.
5,203,768       04/1993    Haak et al. --
"5,084,008" reference, the correct spelling of the name should be -- Phipps --

Column 8,
Line 44, "e" should read -- $e^-$ --

Column 10,
Line 41, "0.06% wt. NaCl." should read -- 0.06% to about 0.9% wt. NaCl. --

Signed and Sealed this

Seventh Day of September, 2004

JON W. DUDAS
*Director of the United States Patent and Trademark Office*